(12) United States Patent  
Abdurahman et al.

(10) Patent No.: US 9,569,864 B2  
(45) Date of Patent: Feb. 14, 2017

(54) METHOD AND APPARATUS FOR PROJECTION IMAGE GENERATION FROM TOMOGRAPHIC IMAGES

(71) Applicant: SIEMENS AKTIENGESELLSCHAFT, Munich (DE)

(72) Inventors: Shiras Abdurahman, Erlangen (DE); Anna Jerebko, Hausen (DE); Michael Kelm, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 167 days.

(21) Appl. No.: 14/484,504

(22) Filed: Sep. 12, 2014

(65) Prior Publication Data

US 2016/0078645 A1   Mar. 17, 2016

(51) Int. Cl.
*G06T 11/00* (2006.01)
*A61B 6/00* (2006.01)
*A61B 6/03* (2006.01)

(52) U.S. Cl.
CPC .............. *G06T 11/003* (2013.01); *A61B 6/032* (2013.01); *A61B 6/5223* (2013.01); *A61B 6/5205* (2013.01)

(58) Field of Classification Search
None
See application file for complete search history.

(56) References Cited

U.S. PATENT DOCUMENTS 5,625,660 A * 4/1997 Tuy .................. G06T 11/006
378/15
8,781,197 B2 * 7/2014 Wang .................... G01R 33/54
382/131

OTHER PUBLICATIONS

Pawel A. Penczek, "Three-dimensional spectral signal-to-noise ratio for a class of reconstruction algorithms," Journal of Structural Biology, 138 (2002): 34-46.*
Rohlfing et al., "Volume-Preserving Nonrigid Registration of MR Breast Images Using Free-From Deformation With an Incompressibility Constraint," IEEE Transactions on Medical Imaging, vol. 22, No. 6, Jun. 2003.*

* cited by examiner

*Primary Examiner* — Matthew Bella
*Assistant Examiner* — Soo Shin
(74) *Attorney, Agent, or Firm* — Laurence Greenberg; Werner Stemer; Ralph Locher

(57) ABSTRACT

A method for generating a projection image from tomographic images first captures (S101) a number of stacked two-dimensional tomographic images representing a tomographic volume. The pixels of the stacked two-dimensional tomographic images are weighted (S102) along a number of projection beams through the tomographic volume with weighting factors that are chosen under the constraint that the sum of all squared weighting factors for each individual projection beam is between a given lower limit and a given upper limit. Then the weighted pixels are summed up (S103) along the number of projection beams for generating the two-dimensional projection image.

15 Claims, 5 Drawing Sheets

METHOD AND APPARATUS FOR PROJECTION IMAGE GENERATION FROM TOMOGRAPHIC IMAGES

BACKGROUND OF THE INVENTION

Field of the Invention

The present invention relates to a method for generating a projection image from tomographic images and a tomography apparatus for generating a projection image.

Computed tomography (CT), as usually X-ray computed tomography, is a widely-used medical diagnostic tool, which allows the generation of tomographic images or slices of an area of interest in a patient. Radiologists often prefer using thick slab or thick-slice volume for diagnostic and screening reading. For example, 5.0 mm slabs are often used for clinical reading and data storage in thoracic CT, although thin, high resolution 0.5 mm slabs are available and used for computer applications such as 3D volume rendering and computer aided diagnosis algorithms.

It is relatively easy to compute 3.0-5.0 mm slabs in thoracic CT images without losing diagnostically relevant information, for example by applying methods such as Average Intensity Projection (AIP) or Maximum Intensity Projection (MIP). The slab thickness is related to the combined thickness of the original slices in the volume. Generally, a slab is rendered as a 2D-image, so that the image can be printed or viewed on a computer screen.

In Digital Breast Tomosynthesis (DBT), data volumes are often reconstructed at a higher resolution, for example at a resolution of 85 microns for a slice thickness of 1.0 mm.

Such a high-resolution volume allows visualization of the fine clinical details required for accurate medical diagnosis of breast cancer, for example microcalcifications of only 100 microns in size, fine spiculations of masses, etc.

A correct depiction of microcalcification morphology and spiculations is critical for the radiologist in order to be able to differentiate between benign and malignant lesions in breast tissue. This means that the amount of data in DBT volumes is large. For example, the total volume of data for a single patient (e.g. including two DBT views and projection images) can exceed one gigabyte. The large data volume complicates data transfer and increases radiologist workload.

Another reason for generating slabs from the initial data is that a radiologist often needs to evaluate the distribution of an entire cluster of calcifications embedded in the surrounding tissue, including any masses and architectural distortions in that region. In breast tissue, a lesion can often extend over 10.0 mm or more, and can extend in any random direction. Therefore, in order to be able to perform such an evaluation, a radiologist should be provided with very thick slabs, i.e. slabs with a thickness in excess of 10.0 mm. In some cases, it might be desirable to perform such an evaluation over the total volume MIP (substantially the whole volume collapsed into a single slab).

However, the usual techniques of reducing the data volume—for example using AIP to merge slices into slabs—are generally associated with a loss of diagnostic information. A slab is rendered as a 2D image, so that 3D information recorded in a series of 2D slices is effectively 'collapsed' into two dimensions.

However, a slab covering a thickness of 2.0 mm or more already suffers from a reduction in contrast and blurred edges of fine calcifications. In a slab covering a thickness of 3.0 mm or more, the edges of masses, spiculations and architectural distortions can be so blurred that the diagnostic usefulness of the slab is severely reduced, and the likelihood of a positive or negative misdiagnosis is increased.

Using MIP to generate the slabs can preserve the calcifications, but the finer structural details and the sharpness and contrast of masses and architectural distortions deteriorate significantly even at slab thickness less than 3.0 mm. However, greater slab thicknesses in excess of 3.0 mm are desirable on account of the reduction in data volume and in order to facilitate data transfer, but the loss of diagnostic information associated with the conventional methods make these methods unsuitable for generating such thick slabs.

For an information-preserving way of computing thick slabs, normalized weighted projections can be used, which compute a weighted average along a projection ray, like given by formula (1):

$$S(u,v) = \int f(\underline{x}(u,v,t)) w(\underline{x}(u,v,t)) dt, \text{ with } \int w(\underline{x}(u,v,t)) dt = 1$$
$$\text{and } w(\underline{x}(u,v,t)) \geq 0, \quad (1)$$

where $\underline{x}(u,v,t)$ describes the 3D-coordinates of a projection ray, $f(\underline{x})$ is the tomographic volume, $w(\underline{x})$ is a weight volume and $S(u,v)$ denotes the constructed thick slab.

BRIEF SUMMARY OF THE INVENTION

It is an object of the present invention to improve the generation of a two-dimensional projection images in terms of sharpness and contrast.

This object is solved by the subject-matter according to the independent claims. Preferred subject-matter is described in the dependent claims, the specification and the drawings.

According to a first aspect this object is solved by a method for generating a projection image from tomographic images, comprising the steps of capturing a number of stacked two-dimensional tomographic images representing a tomographic volume; weighting pixels of the stacked two-dimensional tomographic images along a number of projection beams through the tomographic volume with weighting factors chosen under the constraint that the sum of all squared weighting factors for each individual projection beam is between a given lower limit and a given upper limit; and summing up the weighted pixels along the number of projection beams for generating the two-dimensional projection image. The method can additionally comprise the step of displaying the projection image on a screen. By using the aforementioned constraint noise properties of a constructed thick slab are homogenized. The projection image contains more details.

In a preferred embodiment of the method the weighting factors are determined on the basis of predetermined initial weighting factors. In this embodiment the weighting factors can be determined fast with low computational power.

In further preferred embodiment of the method the sum of all squared initial weighting factors is lower than the given lower limit or higher than the given upper limit. In this embodiment the initial weighting factors can be easily modified to comply with the constraint.

In further preferred embodiment of the method the weighting factors are determined on the basis of a loss function that penalizes differences between the respective initial weighting factor and the weighting factor. In this embodiment a fast solution of the weighting factors is found.

In further preferred embodiment of the method the loss function is based on the squared difference between the weighting factor and the initial weighting factor. In this embodiment the loss function can be calculated easily with a few steps.

In further preferred embodiment of the method the weighting factors are modified by an optimization method such that the sum of the loss function for each weighting factor is minimized. In this embodiment noise is reduced effectively.

In further preferred embodiment of the method the given lower limit is equal to the given upper limit. In this embodiment noise is equally homogenized over all tomographic images and computational costs can be reduced.

In further preferred embodiment of the method the weight factors are chosen such that the set of all weighting factors has an exact number of non-zero weight factors. In this embodiment a sparse weighting vector is found and a sharp projection image is generated.

In further preferred embodiment of the method the non-zero weight factors are chosen from a given discrete set of weight factors. In this embodiment only few calculation steps are required for finding a solution.

In further preferred embodiment of the method a given number of top initial weighting factors is replaced by a corresponding number of predetermined non-zero weighting factors and the remaining initial weighting factors are set to zero. In this embodiment also only few calculation steps are required for finding a solution.

In further preferred embodiment of the method a brute force approach is used on the basis of a number of discrete weighting factors for finding weighting factors fulfilling the constraint that the sum of all squared weighting factors is between a given lower limit and a given upper limit. In this embodiment a solution is found leading to an extremely detailed projection image.

In further preferred embodiment of the method the set of weighting factors comprises at most a given number of non-zero weighting factors. In this embodiment a sparse weighting vector is used and a sharp projection image is generated.

In further preferred embodiment of the method the weighting factor for a first pixel is larger than a weighting factor of a second pixel for all pixels along the projection beam. In this embodiment arbitrary permutations can be considered for a minimizing solution.

In further preferred embodiment of the method the weight factors are sorted by their size. In this embodiment arbitrary permutations can also be considered for a minimizing solution.

According to a second aspect this object is solved by a tomography apparatus for generating a projection image, comprising an imaging means for capturing a number of stacked two-dimensional tomographic images representing a tomographic volume; a weighting means for weighting pixels of the stacked two-dimensional tomographic images along a number of projection beams through the tomographic volume with weighting factors chosen under the constraint that the sum of all squared weighting factors for each individual projection beam is between a given lower limit and a given upper limit; and a summing means for summing up the weighted pixels along the number of projection beams for generating the two-dimensional projection image. Thereby the same advantages as by the method are achieved.

DETAILED DESCRIPTION OF THE INVENTION

Figure 1:
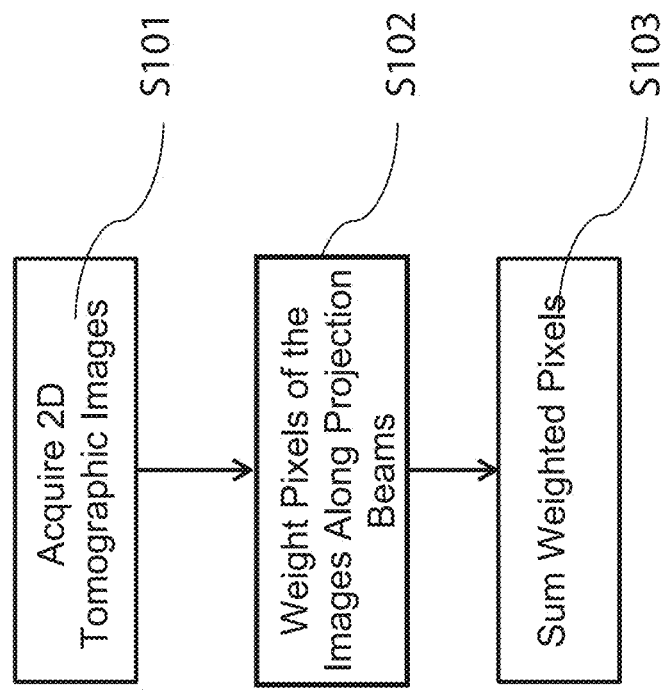
FIG. 1 shows a diagram of the singles steps of the method.

FIG. 1 shows a diagram of the singles steps of the method. In a first step S101 a number of stacked two-dimensional tomographic images representing a tomographic volume is detected by a tomography apparatus.

If discretized, equation (1) can be formulated as a normalized sum $$S(u,v) = \sum_{n=1}^{N} f(\underline{x}_n) w_n, \text{ with } \sum_{n=1}^{N} w_n = 1 \text{ and } w_n \geq 0, \quad (2)$$

where $\underline{x}_n = \underline{x}(u,v,t_n)$ is a suitable discretization of the projection ray and $w_n = w(\underline{x}_n)$.

Using such a weighted average, more weight can be given to tomographic structures in the volume that are to be emphasized in the thick slab. In order to avoid overlapping tissue and blurring, sparse weights should be chosen in the sense that most weighting factors $w_n$ are zero. In one extreme, only one weighting factor $w_n$ is non-zero which then needs to equal 1 due to the constraint that all the weighting factors sum to 1. In another extreme, all weighting factors are equal and then need to be 1/N, which results in the usual AIP projection.

When constructing thick slabs with varying weighting factors according to formula (1) or (2), the resulting projection image may consist of blurred and low-noise regions (e.g. $w_n = 1/N$) as well as very sharp and high-noise regions (e.g. one $w_n = 1$). This yields an artificial impression of the projection image. Thus, the weighting factors $w_n$ are constrained in a way that ensures similar levels of noise throughout the entire thick slab.

Assuming the tomographic volume exhibits white, additive homoscedastic noise, i.e.

$$f(\underline{x}_n) = \bar{f}(\underline{x}_n) + \xi_n, \text{ with } E[\xi_n]=0, E[\xi_n^2]=\sigma^2 \text{ and } E[\xi_i \xi_j]=0 \quad (3)$$

where $\bar{f}(\underline{x}_n)$ is the tomographic image without noise, $\xi_n$ is a random variable and E[.] denotes the expected value. With formula (2), the variance of the tick slab can then be computed as $$\text{Var}(S(u,v)) = E[(S(u,v) - E[S(u,v)])^2] = E[(\sum_{n=1}^{N} \xi_n w_n)^2]$$
$$= \sigma^2 \sum_{n=1}^{N} w_n^2 \quad (4)$$

Formula (4) shows that with the two extreme choices of the weighting factors, the resulting noise level in the composite slab varies between $\sigma^2$ for one $w_n=1$ and $\sigma^2/N$ for all $w_n=1/N$. Thus, in order to obtain a thick slab with equal noise in every pixel (u,v) the sum of squared weighting factors $\sum_{n=1}^{N} w_n^2$ has to be equal for all projections. In practice, slight variations in noise level are not perceivable which means that small variations can be tolerated. Thus the sum of squared weighting factors is constrained to:

$$\alpha \leq \sum_{n=1}^{N} w_n^2 \leq \beta, \quad (5)$$

which includes the case of equality for $\alpha = \beta$. Consequently in a second step S102 pixels of the stacked two-dimensional tomographic images along a number of projection beams through the tomographic volume are weighted with the individual weighting factor $w_n$ which is chosen under the constraint that the sum of all squared weighting factors is between a given lower limit and a given upper limit. The geometry of the projection beam can be an orthographic geometry, a cone beam geometry or a fan geometry. Thus, each pixel from the two-dimensional tomographic images lying on a particular projection beam is weighed with the individual weighting factor $w_n$. The respective pixel is given by the crossing point of the projection beam with the layer of the stacked two-dimensional tomographic image.

In a third step S103 the weighted pixels along the number of projection beams are summed up for generating the two-dimensional projection image. Thereby the noise properties of the constructed thick slab in such an approach are explicitly considered.

When given some weight volume that does not obey constraint (5), e.g. computed using a CAD system, using edge information, entropy or similar, a new set of similar weighting factors is to be found that obeys constraint (5). New weighting factors $w_n$ can be found from the given initial weighting factors $a_n$ by solving the constrained minimization problem $$\min_{w_n} \Sigma_{n=1}^{N} l(w_n, a_n) \quad (6)$$

such that $$\alpha \leq \Sigma_{n=1}^{N} w_n^2 \leq \quad (7)$$

$$\Sigma_{n=1}^{N} w_n = 1 \text{ and} \quad (8)$$

$$w_n \geq 0 \forall n, \quad (9)$$

where the loss function $l(w_n, a_n)$ penalizes differences between the new and given initial weighting factors, for example $l(w_n, a_n) = (w_n - a_n)^2$. However, other robust loss functions are conceivable.

Figure 2:
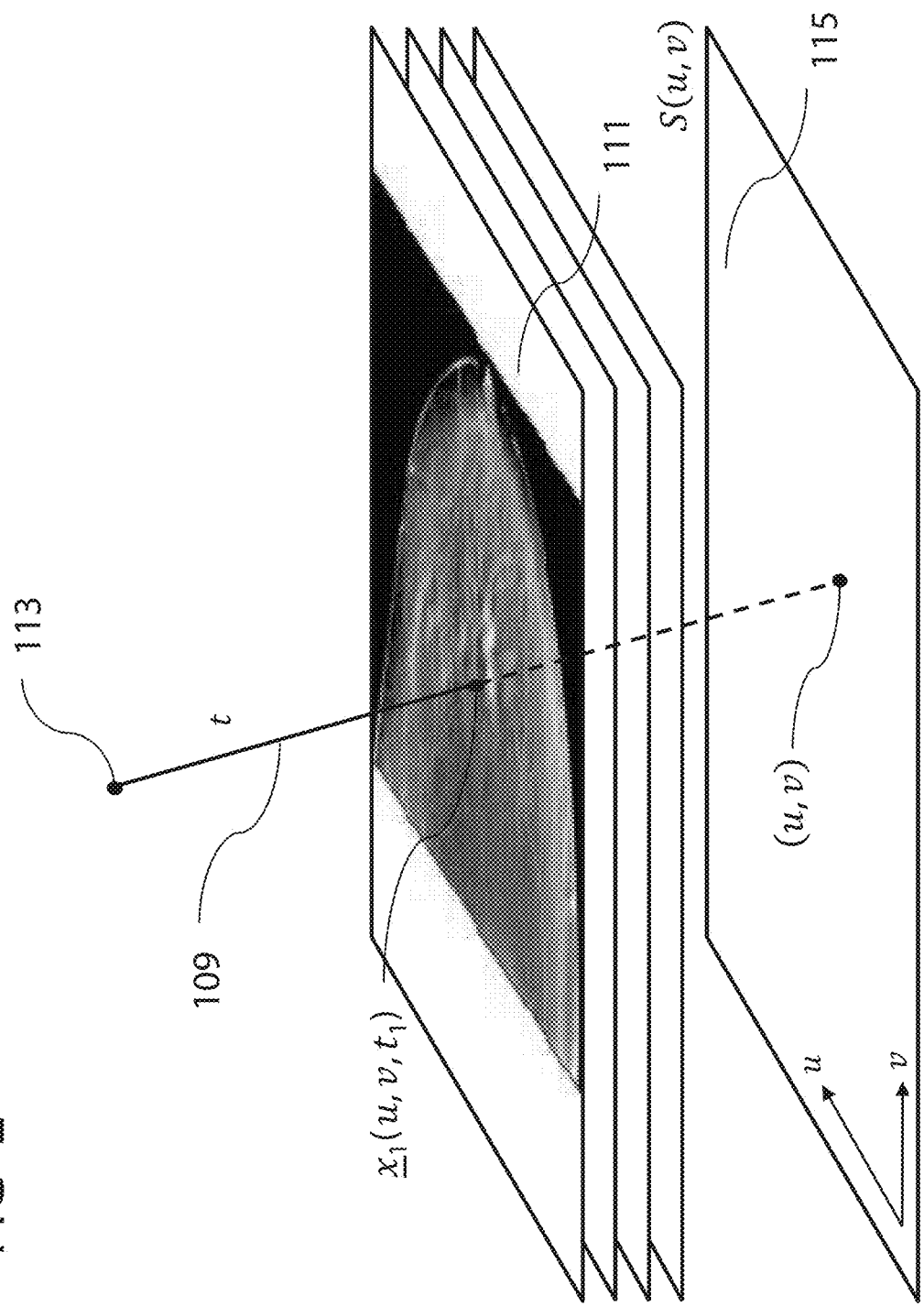
FIG. 2 shows a schematic view of a projection beam and a two-dimensional tomographic image.

FIG. 2 shows a schematic view of a projection beam 109 and a two-dimensional tomographic image 111, which is the first of a stack of two-dimensional tomographic images. The projection beam 109 starts at a projection center 113 and crosses the plane of the two-dimensional tomographic image 111 at point $x_1$ (u, v, $t_1$). The pixel at point $x_1$ (u, v, $t_1$) is weighted with a weighting factor $w_1$. This is repeated for all further crossing points with the additional tomographic images. The projection beam 109 ends at a virtual detector 115. The point (u, v) defines a pixel of the virtual detector 115 whose intensity S(u, v) is computed as weighted sum of pixels of the stacked two-dimensional tomographic images 111 along the projection ray 109.

Figure 3:
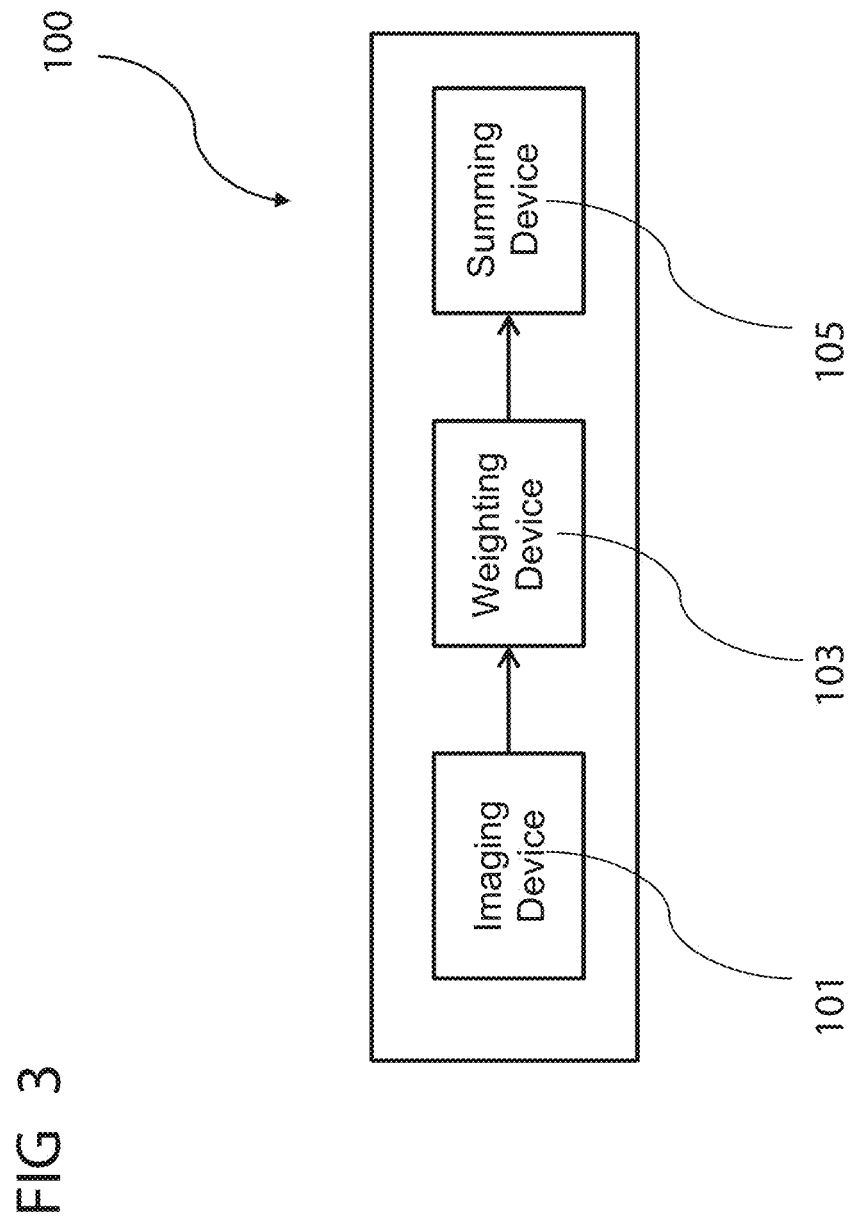
FIG. 3 shows a schematic view of a tomography apparatus.

FIG. 3 shows a schematic view of a tomography apparatus 100. The tomography apparatus 100 can be a computer tomography apparatus for examination of a human breast, like mammographic devices as a diagnostic and a screening tool. The tomography apparatus 100 serves for imaging of a human body by sections or sectioning, through the use of any kind of penetrating wave. A computer tomography apparatus relates to a technology that uses computer-processed x-rays to produce tomographic images (virtual slices) 111 of specific areas of the scanned object, allowing the user to see what is inside it without cutting it open.

The tomography apparatus 100 is additionally capable of generating a projection image from two-dimensional tomographic images 111 representing a tomographic volume. In particular, the tomography apparatus 100 comprises an imaging means 101 for detecting a number of stacked two-dimensional tomographic images 111 representing a tomographic volume; a weighting means 103 for weighting pixels of the stacked two-dimensional tomographic images 111 along a number of projection beams 109 through the tomographic volume with weighting factors chosen under the constraint that the sum of all squared weighting factors for each individual projection beam is between a given lower limit and a given upper limit; and a summing means 105 for summing up the weighted pixels along the number of projection beams 109 for generating the two-dimensional projection image. In addition the tomography apparatus 100 can comprise a display or screen for displaying the projection image.

The imaging means 101, the weighting means 103 and the summing means 105 can be implemented by a computer with a microprocessor and a data storage that is capable of processing the stacked two-dimensional tomographic images 111 and performing the described operations.

Figure 4:
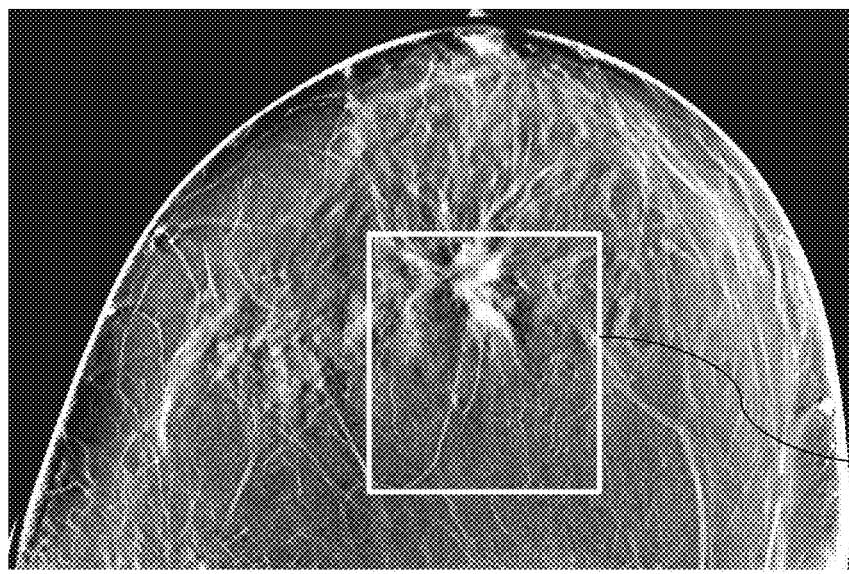
FIG. 4 shows a projection image with and without using a constraint for weighting.
Figure 4:
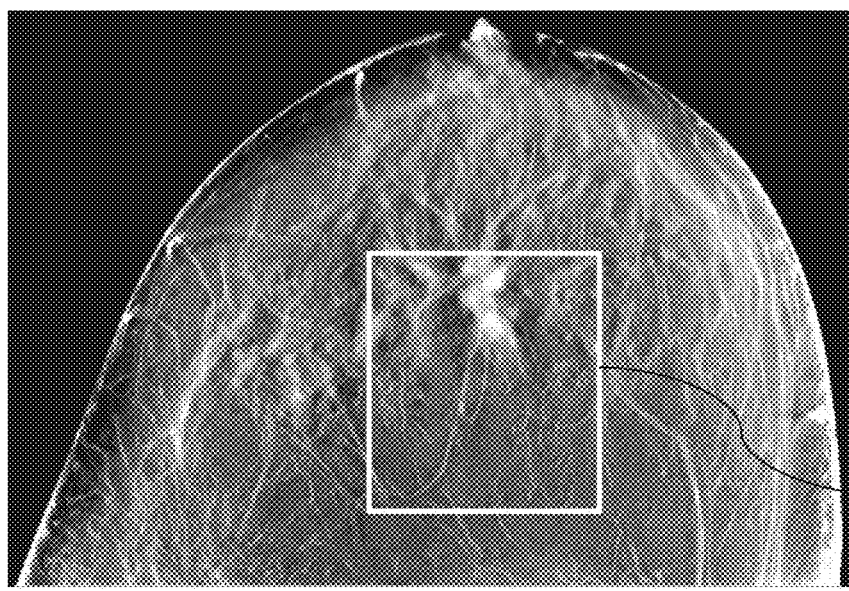

FIG. 4 shows a projection image with and without using a constraint for weighting the pixels along the projection beam 109. The left side of FIG. 3 shows a projection image without weighting by means of the aforementioned constraints. The right side of FIG. 3 shows a projection image with weighting by means of the aforementioned constraints. The projection image on the right side exhibits more details and higher contrast than the projection image on the left side. In the projection image on the right side the noise properties of the constructed thick slab are homogenized. The rectangles denote an image section 107.

Figure 5:
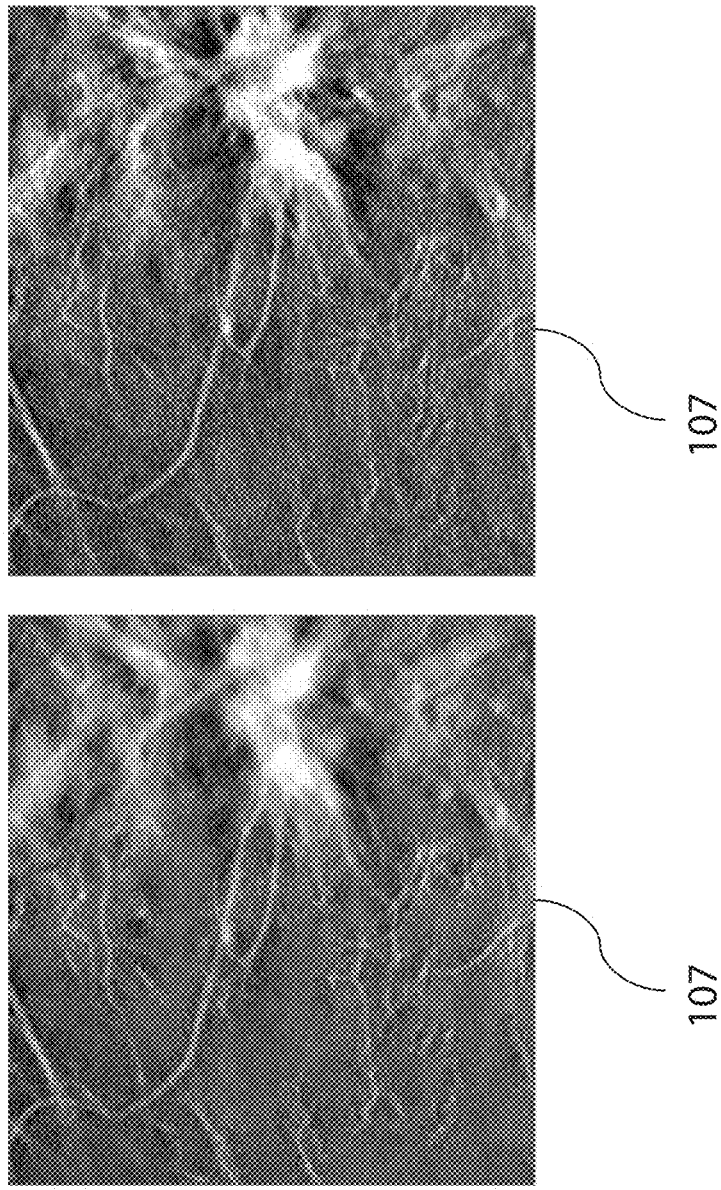
FIG. 5 shows an enlarged projection image with and without using a constraint for weighting.

FIG. 5 shows an enlarged projection image with and without using a constraint for weighting the pixels within the image sections 107. The right image section 107 exhibits more details than the left image section 107.

A solution for formulas (6)-(9) can be found by standard numerical optimization methods. Depending on the type of loss function, e.g. convex vs. non-convex, more or less efficient solvers can be employed. Even explicit solutions derived from the Karush-Kuhn-Tucker (KKT) conditions can be derived for the formulas (6)-(9) or subclasses thereof.

Since the optimization has to take place for every projection, its computational costs can be improved when an efficient solvable subclass is employed, e.g. $l(w_n, a_n) = (w_n - a_n)^2$ and $\alpha = \beta$.

Additional constraints can be imposed by requiring that the weight vector $\underline{w} = [w_n]_{n=1}^{N}$ has exactly Z non-zero entries from a given set of weighting factors, e.g., {0.5, 2, 1, 1, 1} with Z=5. Each such weight vector satisfies constraints (7)-(9) ($\alpha = \beta = 0.32$). An optimal solution for any semiconvex loss function, e.g. $l(w_n, a_n) = (w_n - a_n)^2$ but also L1 or Huber, is found by replacing the top Z initial weight factors $a_n$ with the Z given non-zero weight factors (ordered by size) and setting the remaining initial weight factors to zero.

A set of candidate solution weighting vectors $W = \{\underline{w}_k\}_{k=1}^{K}$ that satisfies conditions (7)-(9) can be computed once before the optimization is done for all projections. A brute-force approach considers a discrete number L of weighting factors, e.g. $w_n \xi \{0, 0.01, 0.02, \ldots, 1\}$ (L=101) for each weighting factor. Since this can yield a huge number of candidate solutions (O($L^N$)). However, additional constraints can be applied during candidate generation:

(C3.1) To promote sparse weight vectors, only weight vectors $\underline{w}_k$ with up to Z non-zero weight entries are accepted.

(C3.2) Since the terms of the sums in (6), (7) and (8) can be arbitrarily permuted, the additional constraint $w_n \geq w_{n+1}$ is applied to further limit the amount of candidate solution vectors.

For every projection with a given weight vector $\underline{a} = [a_n]_{n=1}^{N}$ a weight vector $\underline{w}_k$ is then chosen from the set of candidate solutions W which minimizes formula (6) for a given loss function. During the search for a minimizing solution, arbitrary permutations of the candidate solutions in W have to be considered due to the constraint (C3.2). This can be achieved by an approach like in solution 2, where the weighting factors are sorted by size.

The scope of the invention is defined by the claims and is not restricted by special features discussed in the description or shown in the figures. All features discussed with respect to different embodiments can be combined variously and independently in order to simultaneously realize their technical effect.

REFERENCE SIGNS 100 tomography apparatus
101 imaging means
103 weighting means
105 summing means
107 image section
109 projection beam
111 tomographic images
113 virtual projection center
115 virtual detector

The invention claimed is:

1. A method for generating a projection image from tomographic images, the method comprising the following steps:
capturing a plurality of stacked two-dimensional tomographic images representing a tomographic volume;
weighting pixels of the stacked two-dimensional tomographic images along a number of projection beams through the tomographic volume with weighting factors chosen under a constraint that a sum of all squared weighting factors for each individual projection beam lies between a given lower limit and a given upper limit, the given lower limit set equal to the given upper limit; and
generating the two-dimensional projection image by summing up the weighted pixels along the number of projection beams.

2. The method according to claim 1, which comprises determining the weighting factors on a basis of predetermined initial weighting factors.

3. The method according to claim 2, wherein a sum of all squared initial weighting factors is less than the given lower limit or higher than the given upper limit.

4. The method according to claim 2, which comprises determining the weighting factors on the basis of a loss function that penalizes differences between the respective initial weighting factor and the weighting factor.

5. The method according to claim 4, wherein the loss function is based on the squared difference between the weighting factor and the initial weighting factor.

6. The method according to claim 2, wherein a given number of top initial weighting factors is replaced by a corresponding number of predetermined non-zero weighting factors and the remaining initial weighting factors are set to zero.

7. The method according to claim 1, which comprises employing an approach that considers a discrete number of weighting factors for finding weighting factors fulfilling the constraint that the sum of all squared weighting factors lies between the given lower limit and the given upper limit.

8. The method according to claim 7, wherein the set of weighting factors comprises at most a given number of non-zero weighting factors.

9. The method according to claim 7, wherein the weighting factor for a first pixel is larger than a weighting factor of a second pixel for all pixels along the projection beam.

10. The method according to claim 9, which comprises sorting the weighting factors according to a size thereof.

11. A method for generating a projection image from tomographic images, the method comprising the following steps:
capturing a plurality of stacked two-dimensional tomographic images representing a tomographic volume;
weighting pixels of the stacked two-dimensional tomographic images along a number of projection beams through the tomographic volume with weighting factors chosen under a constraint that a sum of all squared weighting factors for each individual projection beam lies between a given lower limit and a given upper limit;
generating the two-dimensional projection image by summing up the weighted pixels along the number of projection beams;
determining the weighting factors on the basis of a loss function; and
modifying the weighting factors by an optimization method in order to minimize the sum of the loss function for each weighting factor.

12. A method for generating a projection image from tomographic images, the method comprising the following steps:
capturing a plurality of stacked two-dimensional tomographic images representing a tomographic volume;
weighting pixels of the stacked two-dimensional tomographic images along a number of projection beams through the tomographic volume with weighting factors chosen under a constraint that a sum of all squared weighting factors for each individual projection beam lies between a given lower limit and a given upper limit, the weighting factors chosen such that a set of all weighting factors has an exact number of non-zero weighting factors; and
generating the two-dimensional projection image by summing up the weighted pixels along the number of projection beams.

13. The method according to claim 12, wherein the non-zero weight factors are chosen from a given discrete set of weight factors.

14. The method according to claim 13, wherein a given number of top initial weighting factors is replaced by a corresponding number of predetermined non-zero weighting factors and the remaining initial weighting factors are set to zero.

15. A tomography apparatus for generating a projection image, comprising:
an imaging device configured to perform the method of claim 1 for capturing a number of stacked two-dimensional tomographic images representing a tomographic volume;
a weighting device for weighting pixels of the stacked two-dimensional tomographic images along a number of projection beams through the tomographic volume with weighting factors chosen under a constraint that a sum of all squared weighting factors for each individual projection beam lies between a given lower limit and a given upper limit; and
a summing device generating the two-dimensional projection image by summing up the weighted pixels along the number of projection beams.

* * * * *